(12) United States Patent
Hartmann et al.

(10) Patent No.: US 12,708,260 B2
(45) Date of Patent: Aug. 18, 2026

(54) PHOROPTER AND OPTOMETRY DEVICE FOR TESTING AN INDIVIDUAL'S EYES

(71) Applicant: Essilor International, Charenton-le-Pont (FR)

(72) Inventors: Léonard Hartmann, Charenton-le-Pont (FR); Stéphane Boutinon, Charenton-le-Pont (FR); Bernard Brechemier, Charenton-le-Pont (FR); Arnaud Mesnier, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 525 days.

(21) Appl. No.: 18/003,384

(22) PCT Filed: Jun. 23, 2021

(86) PCT No.: PCT/EP2021/067236
§ 371 (c)(1),
(2) Date: Dec. 27, 2022

(87) PCT Pub. No.: WO2022/002729
PCT Pub. Date: Jan. 6, 2022

(65) Prior Publication Data

US 2023/0309817 A1 Oct. 5, 2023

(30) Foreign Application Priority Data

Jun. 29, 2020 (EP) .................................... 20315327

(51) Int. Cl.
*A61B 3/028* (2006.01)
*A61B 3/032* (2006.01)
(Continued)

(52) U.S. Cl.
CPC ............ *A61B 3/0285* (2013.01); *A61B 3/032* (2013.01); *A61B 3/08* (2013.01); *A61B 3/103* (2013.01); *A61B 3/14* (2013.01)

(58) Field of Classification Search
CPC ......... A61B 3/0285; A61B 3/032; A61B 3/08; A61B 3/103; A61B 3/14
See application file for complete search history.

(56) References Cited

U.S. PATENT DOCUMENTS

2002/0159030 A1* 10/2002 Frey .......................... G01J 9/00 351/212
2004/0218143 A1 11/2004 Terabe
(Continued)

FOREIGN PATENT DOCUMENTS

CN 210408381 U 4/2020
EP 1 472 969 A1 11/2004
(Continued)

OTHER PUBLICATIONS

International Search Report mailed on Jan. 17, 2022 in PCT/EP2021/067236 filed on Jun. 23, 2021 (6 pages).
(Continued)

*Primary Examiner* — Sharrief I Broome
*Assistant Examiner* — K Muhammad
(74) *Attorney, Agent, or Firm* — Oblon, McClelland, Maier & Neustadt, L.L.P.

(57) ABSTRACT

A phoropter for testing an individual's eyes when observing a target, the phoropter including two optical units for the two eyes of the individual, each having an entry on the target side, an exit aperture on the individual's side, and an optical system for providing different vision correction powers to the corresponding eye of the individual, moving means adapted to adjust the relative position of the two optical units, a partially reflecting mirror situated between the
(Continued)

Figure 1:
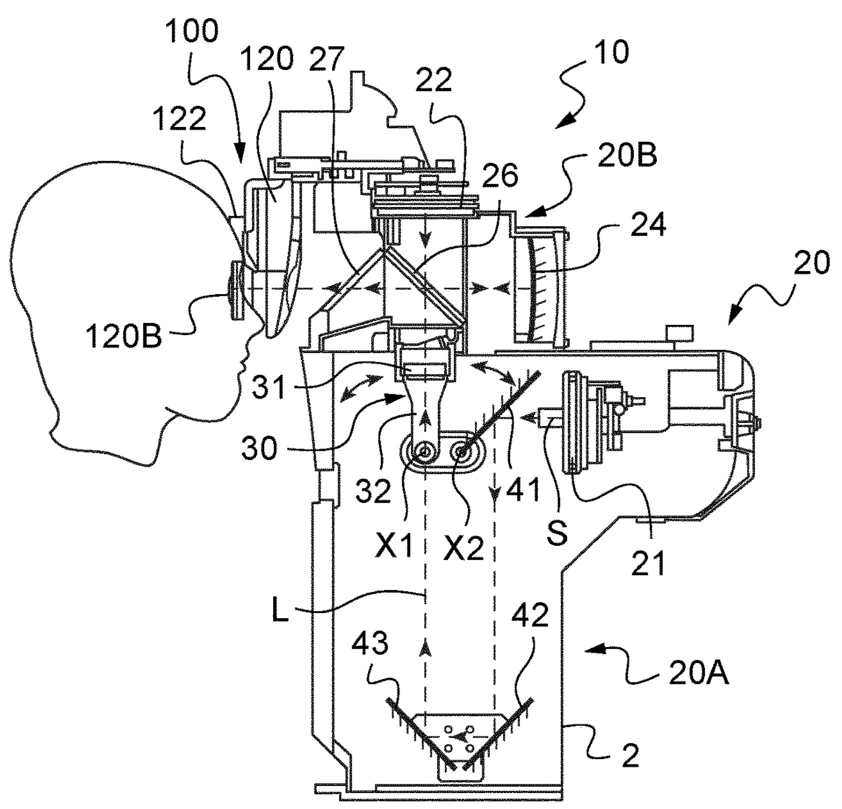

optical units and the target, an image acquiring device directed toward the partially reflecting mirror so as to acquire images of the eyes of the individual looking at the target through the two optical units, and an image displaying device suitable to display the acquired images.

15 Claims, 6 Drawing Sheets

(51) Int. Cl.
*A61B 3/08* (2006.01)
*A61B 3/103* (2006.01)
*A61B 3/14* (2006.01)

(56) References Cited

U.S. PATENT DOCUMENTS

2015/0374233 A1* 12/2015 Zhang ...................... A61B 3/14 351/246
2018/0276819 A1 9/2018 Guo et al.
2019/0069777 A1* 3/2019 Krall .................... A61B 3/0091
2019/0269318 A1* 9/2019 Takii .................... A61B 3/1035
2019/0274539 A1* 9/2019 Nauche ................ A61B 3/0041

FOREIGN PATENT DOCUMENTS

EP 3 369 365 A1 9/2018
EP 3 533 383 A1 9/2019
EP 3 711 654 A1 9/2020
JP 8-01227 A 1/1996
JP 2000-131583 A 5/2000
JP 2014128314 A * 7/2014
JP 2015066134 A * 4/2015
JP 2017-176657 A 10/2017
JP 2019062938 A * 4/2019
WO WO 2015/107303 A1 7/2015

OTHER PUBLICATIONS

Combined Chinese Office Action and Search Report issued Mar. 28, 2025, in corresponding Chinese Patent Application No. 202180036533.3 (with English Translation), 18 pages.
Japanese Office Action issued Mar. 25, 2025, in corresponding Japanese Patent Application No. 2022-580350, 3 pages.

* cited by examiner

PHOROPTER AND OPTOMETRY DEVICE FOR TESTING AN INDIVIDUAL'S EYES

TECHNICAL FIELD OF THE INVENTION

The invention relates to a phoropter and to an optometry device for testing an individual's eyes.

BACKGROUND INFORMATION AND PRIOR ART

In the context of the measurement of the visual acuity of a patient, it has already been proposed to simulate the visual compensation to be provided, for example by means of a refractometer (also called phoropter).

Such a phoropter comprises a support element designed to receive the head of the individual and to hold it in a predetermined position relative to a refraction head of the phoropter.

This refraction head houses trial lenses providing different corrections, that can be successively placed in front of the individual's eyes until a suitable correction is found.

In the refraction head, the trial lenses are situated on two discs that are mounted so as to be free to rotate. The rotation is controlled manually. Each disc has to be placed relative to each eye of the patient so that, when one of the discs rotates, the trial lenses of this disc can successively be positioned in front of the corresponding patient's eyes.

Because the patients do not have the same morphology, before trying to simulate the visual compensation to be provided, it is necessary to adjust the position of each disc relative to each eye of the patient.

To this end, the positions of the discs are manually adjustable. Moreover, one of the trial lenses of each disc comprises a reticule that helps the optometrist to place this lens in the axis of the corresponding patient's eye, ensuring thereby a good adjustment of the positions of the discs relative to the positions of the patient's eyes.

The major drawback of such a device is that it needs for the optometrist to observe the patient face-to-face, which is not always possible. Moreover, when the simulation of the visual compensation to be provided has started, the optometrist cannot check if the adjustment is still correct.

SUMMARY OF THE INVENTION

In this context, the present invention provides a phoropter for testing an individual's eyes when observing a target along an optical path, comprising:

- two optical units for the two eyes of the individual, each having an entry on the target side, an exit aperture on the individual's side, and an optical system for providing different vision correction powers to the corresponding eye of the individual,
- moving means adapted to adjust the relative position of the two optical units,
- a partially reflecting mirror situated along the optical path (between the optical units and the target),
- an image acquiring device (for instance one or two cameras) directed toward the partially reflecting mirror so as to acquire images of the eyes of the individual looking at the target through the two optical units, and preferably
- an image displaying device suitable to display the acquired images.

Thanks to the invention, the camera(s) can acquire images of the individual's eyes before the simulation of the visual compensation to be provided or during this simulation. Consequently, the adjustment of the two optical units in front of the two individual's eyes can be done at every moment.

Moreover, the optometrist does not need to observe the patient face-to-face to do this adjustment, enabling the patient to look at the target during this adjustment, which provides a better accuracy in the positioning of the optical units.

According to further non limiting features of the device of the invention:

- said image acquiring device comprises two cameras,
- each camera is directed toward the partially reflecting mirror so as to acquire images of one of the eyes of the individual looking at the target through one of the optical units,
- said moving means comprise a lever to manually adjust the relative position of the two optical units.
- the phoropter also comprises a support element designed to receive the head of the individual and to hold it in position,
- said moving means comprise two levers to manually adjust the positions of the two optical units relative to said support element,
- said moving means comprise at least one motor suitable to adjust the relative position of the two optical units, and a controller programmed to control the motor as a function of the images acquired by the image acquiring device and processed to detect the positions of the individual's pupils,
- said moving means comprise two motors and the controller is programmed to automatically control the motors so as to adjust the positions of the two optical units relative to said support element in the axes of the two individual's pupils,
- said optical system is designed to generate variable spherical powers and variable cylindrical powers,
- said partially reflecting mirror leans along its entire edge on a rim of a frame of a mirror support, said frame comprising three or four tongues that hold the partially reflecting mirror against said rim.

The invention also provides an optometry device for testing an individual's eyes, comprising a phoropter as described here above and a display unit adapted to produce a target, said target being visible through the exit apertures of the two optical units of said phoropter, this display unit comprising:

- a first screen adapted to display a test picture used in producing said visual target, and
- at least one optical element having an optical power,
- said optical element being movable between an active position in which it is placed on an optical path of the light emitted by said first screen and exiting the device through said exit apertures, and a retracted position in which it remains out of said optical path, in order for the target to be produced at a variable distance from said exit apertures.

According to further non limiting features of the optometry device of the invention:

- the device comprises a second screen adapted to display a second picture, an image of this second picture being superimposed with said target at the exit apertures by means of a main partially reflecting mirror,
- a single mirror support holds said main partially reflecting mirror and the partially reflecting mirror of said phoropter,

- said main partially reflecting mirror leans on a rim of a frame of a mirror support,
- said main partially reflecting mirror leans on said rim along its entire edge, a compressible material being sandwiched between said main partially reflecting mirror and said rim.
- said main partially reflecting mirror directly leans on three or four areas projecting from said rim,
- the edge of said main partially reflecting mirror is blocked by three or four pins that take it in sandwich,
- said frame comprises at least two flexible strips that hold said main partially reflecting mirror against said rim,
- said frame lies on a first part of a casing of said mirror support, said casing comprising a second part fixed to the first part and having an abutment that is situated at a distance from the frame, a clearance or a compressible material being provided between the abutment and the frame.

The invention concerns also a mirror support (also called light beam separation box) comprising a casing that supports the main partially reflecting mirror and the partially reflecting mirror.

DETAILED DESCRIPTION OF EXAMPLE(S)

The following description with reference to the accompanying drawings, given by way of non-limiting example makes it clear what the invention consists in and how it can be reduced to practice.

Figure 2:
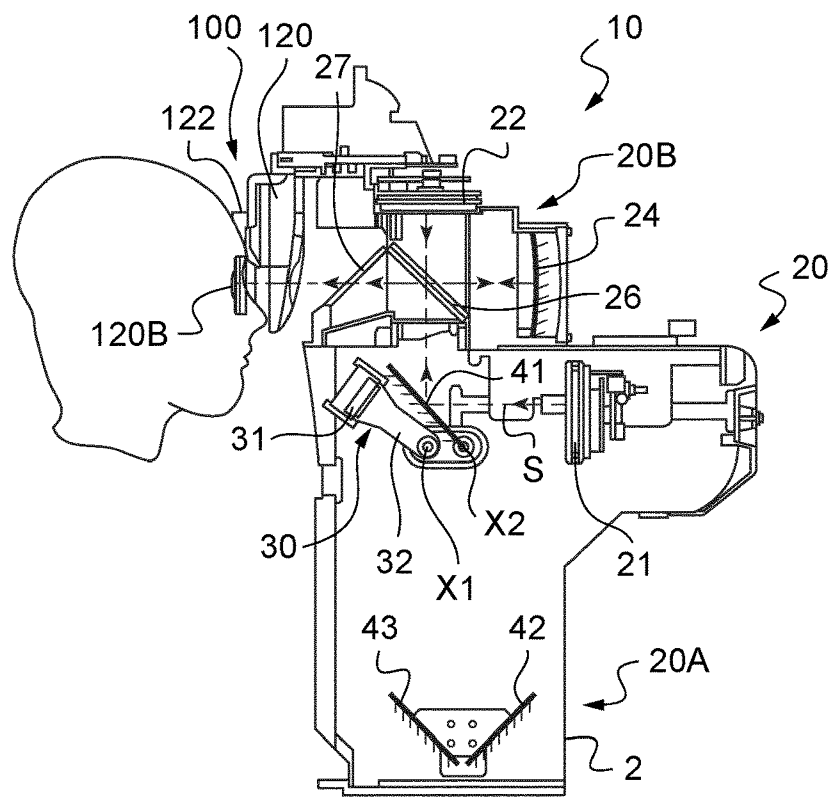
Figure 3:
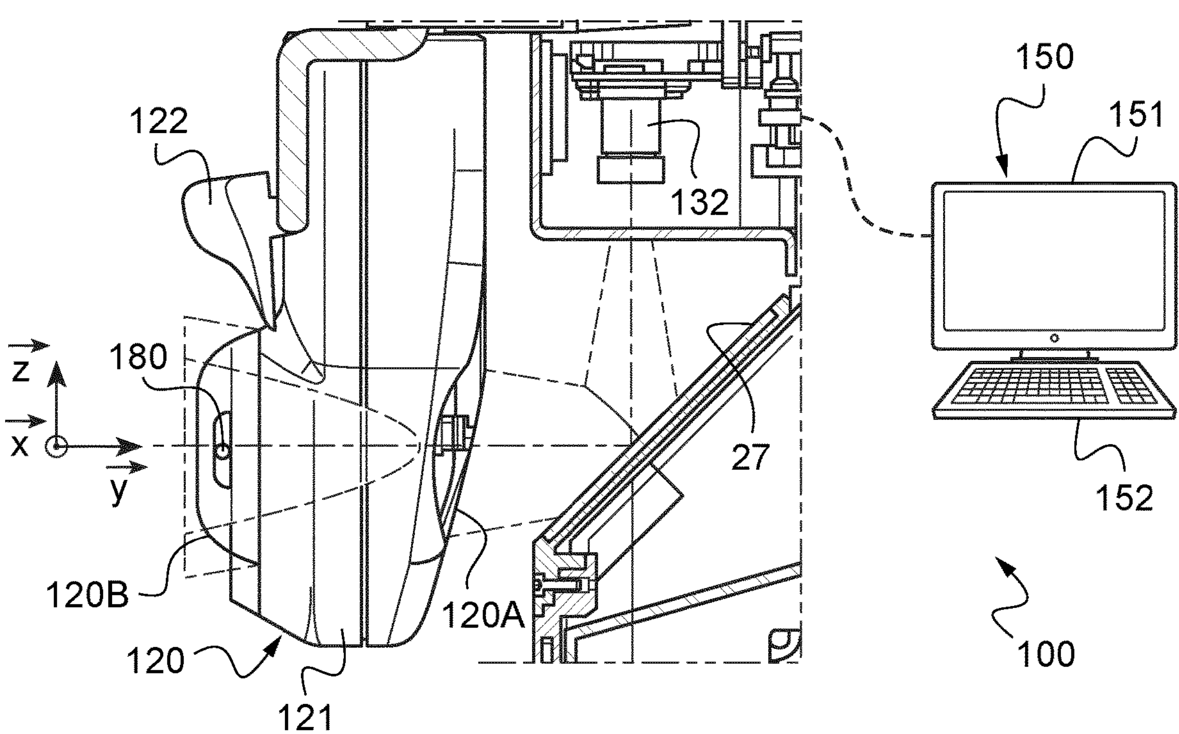
Figure 4:
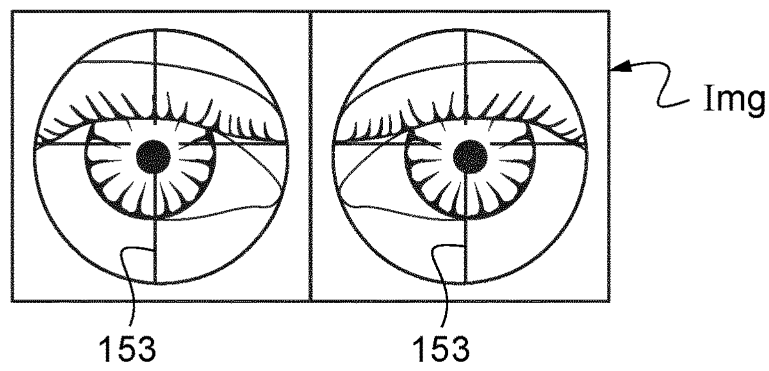
Figure 5:
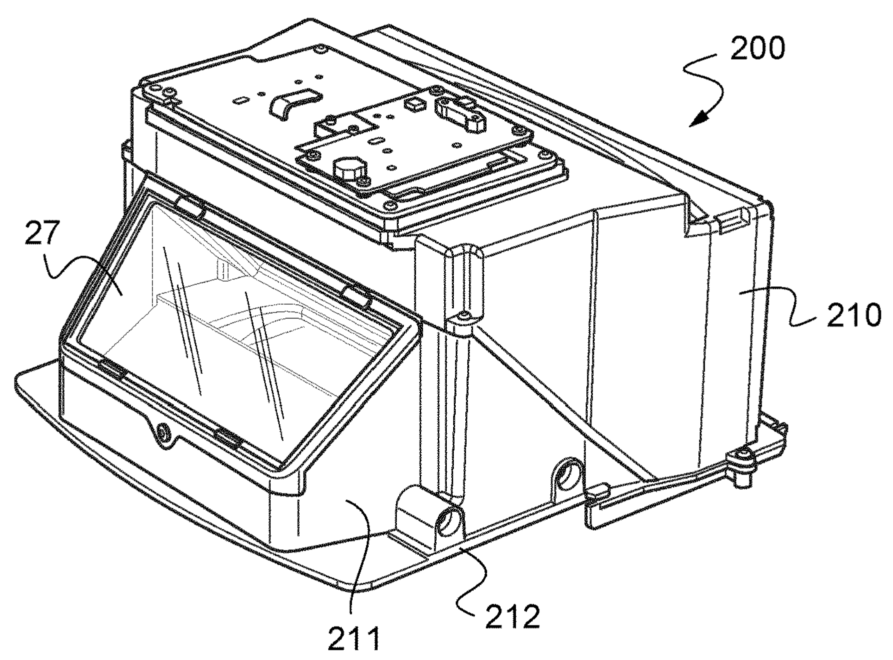
Figure 6:
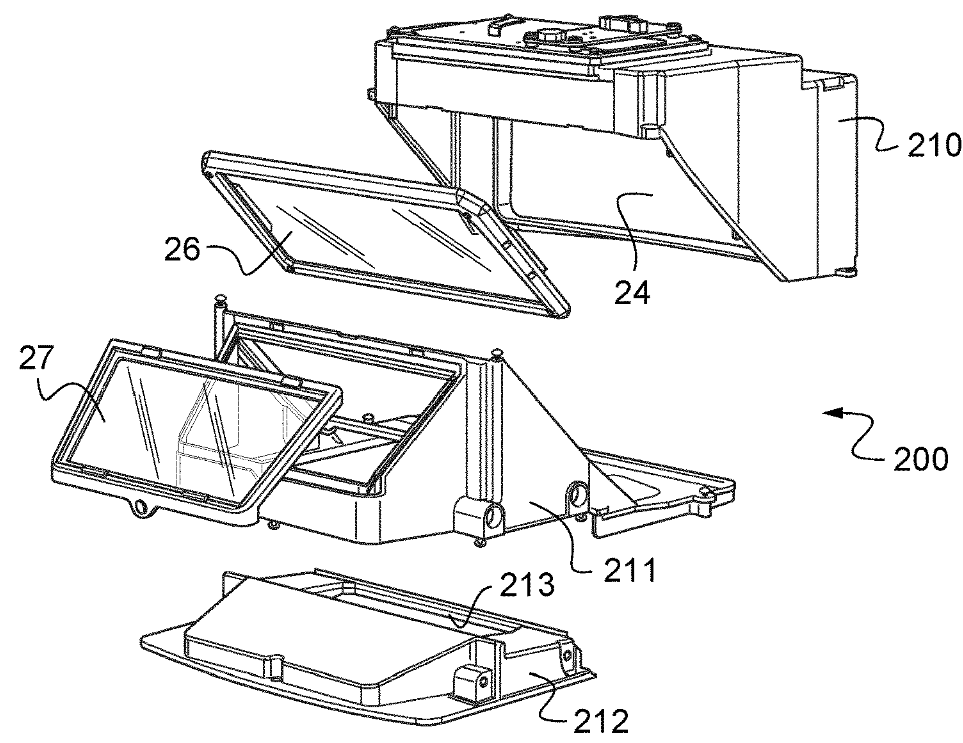
Figure 7:
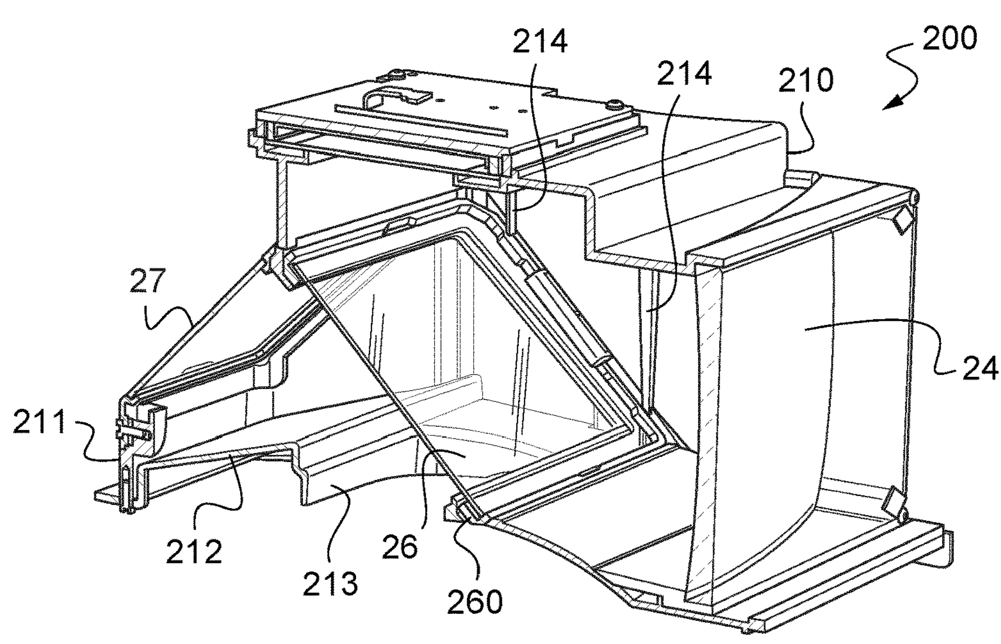
Figure 8:
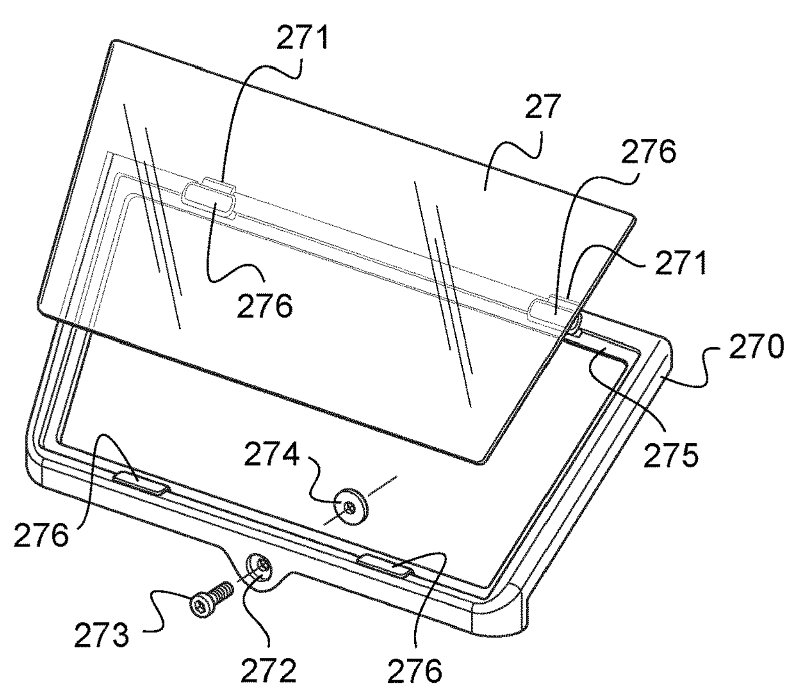
Figure 9:
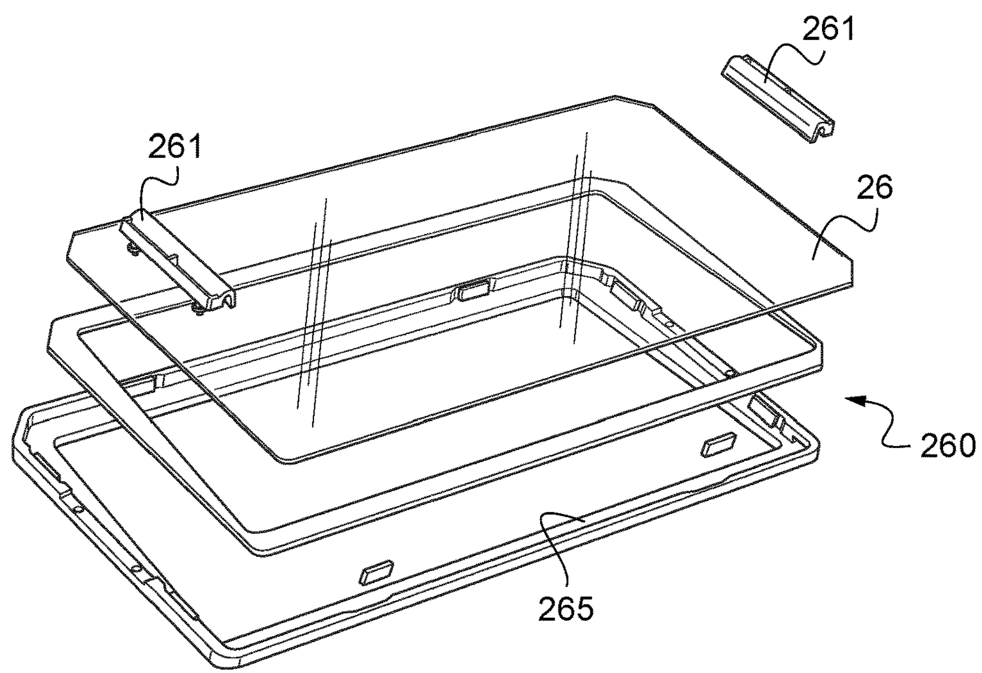
Figure 10:
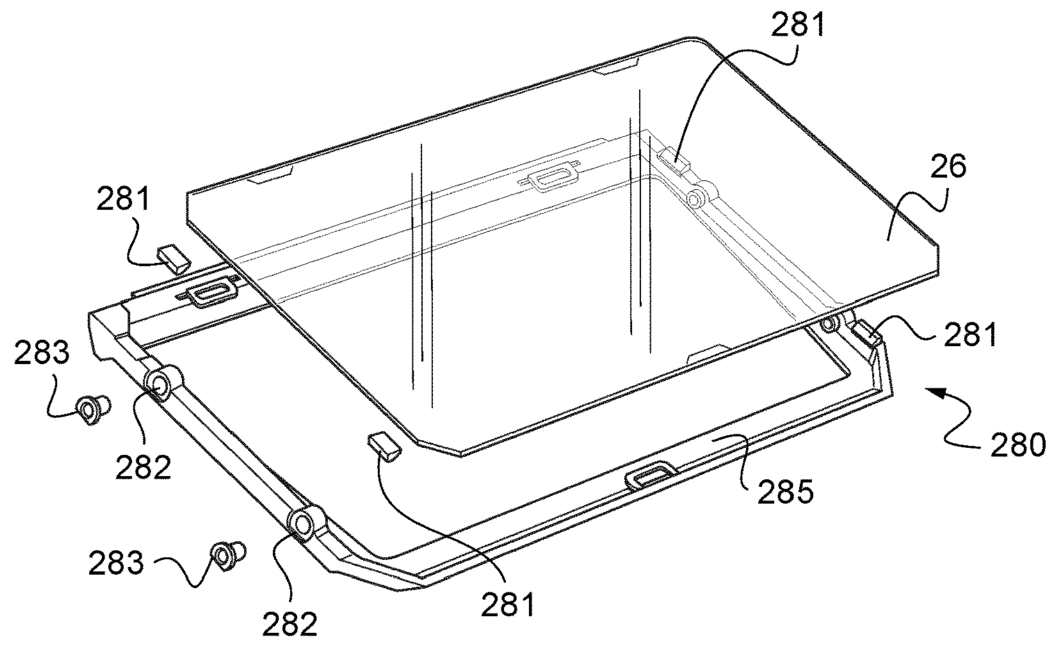
Figure 11:
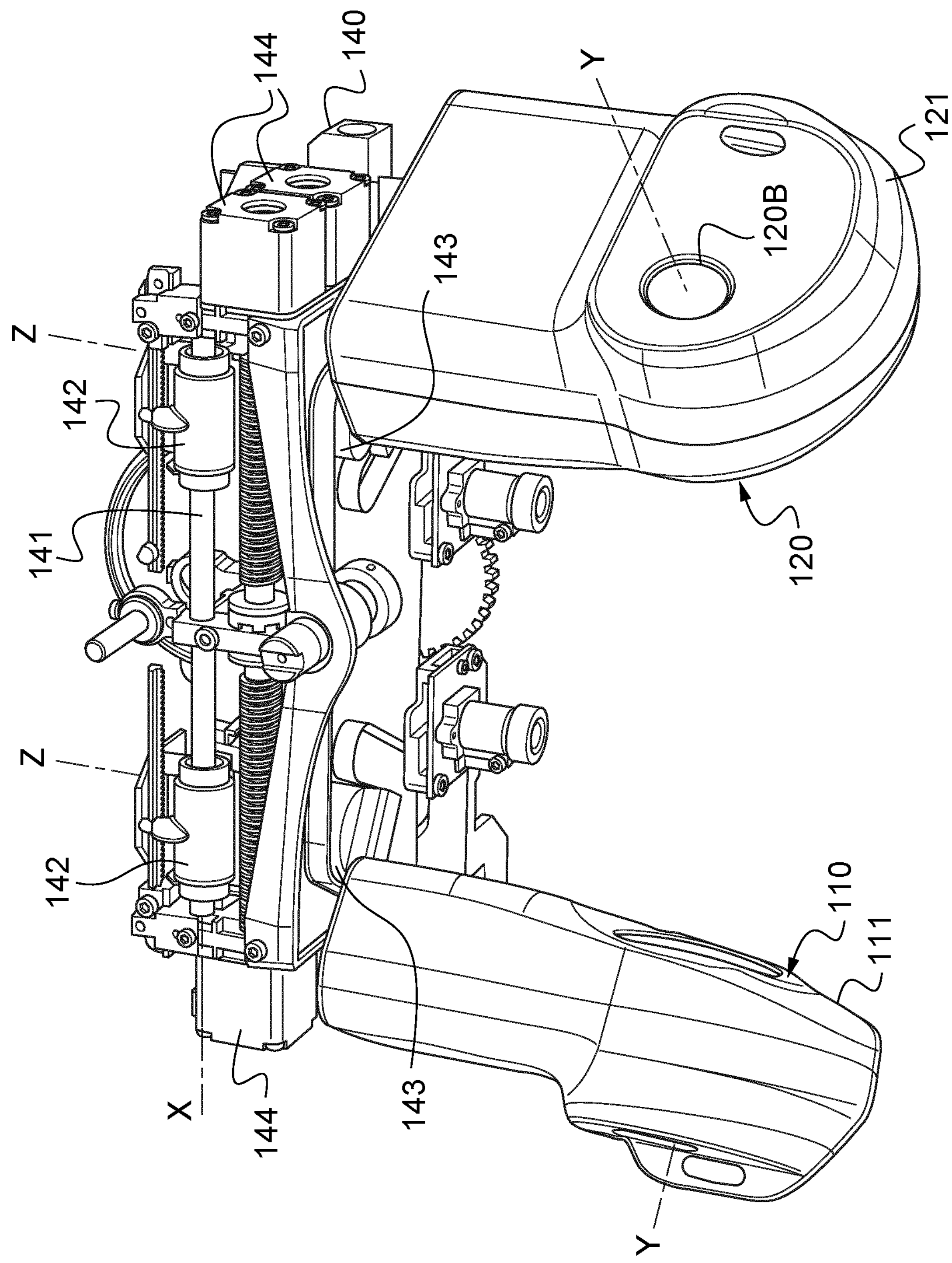

In the accompanying drawings:

FIGS. 1 and 2 represent an optometry device according to the invention,

FIG. 3 is a side view of a phoropter of the optometry device shown in FIGS. 1 and 2, FIG. 4 is an image acquired by the cameras of the phoropter shown in FIG. 3, FIG. 5 is a perspective view of a light beam separation box of the optometry device shown in FIGS. 1 and 2, FIG. 6 is an exploded view of the box of FIG. 5, FIG. 7 is a cross-sectional view of the box of FIG. 5, FIG. 8 is an exploded view of one of the mirrors of the box of FIG. 5, FIG. 9 is an exploded view of another mirror of the box of FIG. 5, according to a first embodiment, FIG. 10 is an exploded view of the other mirror of the box of FIG. 5, according to a second embodiment, FIG. 11 is a perspective view of internal components of the phoropter of FIG. 2.

The invention principally relates to a phoropter (also called "refractometer") designed for providing different vision correction powers close to the eye of the individual. This phoropter could be used with an eye chart placed at 6 meters from the phoropter. But in the described embodiment, this phoropter belongs to an optometry device having a display unit 20 suitable for displaying a test picture to be seen through the phoropter 100. The display unit 20 will be described in a first part of this report. The phoropter 100 will be described after.

In FIGS. 1 and 2, the optical paths of light are represented in dashed lines, the direction of propagation being indicated by arrowheads.

Mobility of the optical component is indicated by double arrows placed beside.

The aim of the optometry device 10 is to test an individual's eyes.

The phoropter 100 is interposed between the display unit 20 and the individual's eye. It is adapted to provide a variable optical correction for the individual's eyes looking therethrough.

The light beam exiting the display unit 20 is directed through the phoropter 100 towards the eye of the individual.

In the shown embodiment, the display unit 20 comprises:

- a screen 21 adapted to display a test picture (a "target") used in producing a visual test image, and
- at least one optical element 30 having an optical power.

Said optical element 30 is movable between an active position in which it is placed on an optical path of the light emitted by said screen and exiting the device through said exit aperture, and a retracted position in which it remains out of said optical path, in order for the visual test image to be produced at a variable distance from said exit aperture 120B.

The optical path is the path that a light beam emitted by the screen 21 at a center of the image displayed by the screen 21 takes in traversing the display unit 20 to reach an exit aperture 120B of the phoropter 100 facing the patient.

When the optical element 30 is in its retracted position (FIG. 2), the visual test image comprises the test picture displayed by said screen 21. The distance between the visual test image and the exit aperture of the phoropter 100 is then the distance measured along said optical path between the exit aperture and the screen 21.

When the optical element is in its active position (FIG. 1), the visual test image comprises an image (or projection) of said test picture displayed by the screen 21 seen through the optical element 30. This image is usually a virtual image. It is located at an optical position. This optical position may for example be at infinity.

The distance between the visual test image and the exit aperture of the phoropter 100 is then the distance between the exit aperture and the optical position of the visual test image. Said optical element 30 may comprise for example an optical lens 31, as in the example described here.

In the case where the optical element 30 comprises an optical lens 31, the image of the test picture is the image of the test picture seen through the lens 31.

The distance between said visual test image and said exit aperture is varied at least between a distance of far vision and a different distance of near or intermediate vision. A distance of far vision is typically comprised between infinity and 65-70 centimeters. A distance of intermediate vision is typically comprised between 65-70 and 40 centimeters. A distance of near vision is typically comprised between 40 and 33 centimeters.

Preferably, the relative positions of the screen 21, the optical element 30 and the exit aperture 120B are adapted to be varied in order for said distance between the visual test image produced and the exit aperture to be continuously varied inside one or several ranges of optical distances between infinity and a near vision distance.

The optometry device 10 includes a main casing 2 adapted to be placed on a table, for instance, or to be mounted on a stand to be placed on a table or on the floor.

The main casing 2 encloses here the display unit 20. The phoropter 100 is mounted on the main casing 2.

The display unit 20 comprises here an acuity module 20A and a scene module 20B.

The acuity module 20A includes the screen 21 and the optical element 30.

The screen 21 produces a light beam along a screen axis S perpendicular to the mean plane of the screen 21. This light beam is meant to produce an image of an object, such as an optotype, for an individual using the optometry device.

In the examples described here, the screen 21 is flat.

The optical element 30 comprises here an achromatic lens, having an effective focal length between 70 centimeters and one meter, preferably of about 80 centimeters, for instance.

Preferably, the optical element 30 and the screen 21 are arranged relative to each other so that there is at least one relative position of the optical lens 31 and the screen 21 for which the screen 21 is placed at a distance from the optical lens 31 equal to the back focal length of said lens 31.

Therefore, in a far vision configuration, while the lens 31 is placed on the optical path of the light, the relative position of said screen 21 and said lens 31 may be adjusted for the screen 21 to be located at a back focal length from said lens 31.

This way, the visual test image generated by the display module 20 may be placed at infinity relative to the exit aperture, and therefore, the eyes of the individual. The distance between the visual test image produced and the exit aperture is then set as infinite.

The optical element 30 comprises the lens 31 and is fixed on a support 32 that is pivotally mounted on part of the casing 2.

In a first angular position of the support 32 of the lens 31, shown in FIG. 1, the support 32 is parallel to the optical path of the light and brings the lens 31 across this optical path: the light emitted by the screen then goes through the lens 31. The optical path of the light follows at least partially the optical axis L of the lens 31.

In a second angular position of the support 32 of the lens 31, shown in FIG. 2, the support 32 is inclined relative to the optical path of the light and brings the lens 31 outside this optical path: the light beam emitted by the screen 21 then avoids going through the lens 31.

The screen 21 is movable in translation along two perpendicular directions for centering said screen 21 relative to the other optical component of the optometry device 10, in particular relative to the optical axis L of said lens 31 in its active position.

This centering step ensures that the light emitted at the center of the screen exits the optometry device at the center of the exit aperture.

In some embodiments the screen 21 may also be movable, in particular along the screen axis S, in order to further vary the distance between the visual test image and the exit aperture.

The acuity module 20A of the display unit 20 also comprises at least one reflecting surface in order to direct the optical path toward the exit aperture 120B.

Said reflecting surface allows folding the optical path of the light beam emitted by the screen, in order to limit the size of the display module.

In practice, the reflecting surface comprises 3 mirrors 41, 42, 43, a first one of which being movable in order to further vary the distance between the visual test image and the exit aperture.

This first mirror 41 is placed on the optical path and mounted to pivot about a rotation axis perpendicular to the optical path of the light beam, in order to be alternatively placed at an angle of 45° or 135° relative to the screen axis S.

Second and third mirrors 42, 43 are disposed at a right angle with respect to each other. In addition, they are disposed at angles of 45° and 135°, with respect to the screen axis S.

Thanks to this arrangement, while the first mirror 41 is in its first position, the light beam produced by the screen 21 may be successively reflected by the first mirror 41 towards the second mirror 42. It is then reflected by the second mirror 42 towards the third mirror 43, then by the third mirror 43, such that it is directed towards the lens 31 along the optical axis L of the lens 31. The screen axis S and said main direction of the optical axis L are here perpendicular to each other.

The light beam goes through the lens 31 (when the optical element 30 is in the first active position) then reaches a first beam splitter 26 and is reflected towards the eye of the individual.

In the configuration shown on FIG. 2, the optical element 30 is in its second retracted position and the first mirror is rotated so that the light beam directly go from the screen 21 to the first beam splitter 26.

The scene module 20B comprises an additional screen 22 and an additional mirror 24. The additional screen 22 is used to display a background picture. This background picture is preferably of an environment familiar to the individual, for example a natural environment, exterior or interior, such as a city, a landscape or a room. The additional mirror 24 is here a concave mirror. Its optical axis goes through the summit of the concave mirror and is here overlapped with the optical axis L of the lens 31 of the acuity module 20A at the exit from the display unit.

The first beam splitter 26 is place between the acuity module 20A and the scene module 20B in order to superimpose the light emitted by the screen 21 of the acuity module 20A and the light emitted by the additional screen 22 of the scene module 20B. The beam splitter 26 is positioned such that it reflects the light coming from the screen 21 of the acuity module 20A towards the phoropter 100 and, ultimately, towards the eye of the individual. It also reflects the light emitted by the additional screen 22 towards the additional mirror 24 and let the light reflected by this first beam splitter 26 go straight through it towards the eye of the individual. Both light beams, coming from the acuity and scene modules exit the casing 2 of the display module through an opening closed by a second beam splitter 27.

Both beam splitter 26, 27 belong to a light beam separation box 200 described hereinafter.

At this step of the description, we can describe in more details the phoropter 100.

This phoropter 100 is shown in FIG. 3.

It includes two optical units (or "phoropter's half-heads") 110, 120 for the two eyes of the individual (only one optical unit 120 is visible in FIG. 3).

These two optical units 110, 120 are here identical.

Each optical unit 110, 120 has a housing 121 including two openings, namely an entry 120A situated on the side of the scene module 20B, and an exit aperture 120B situated on the patient's side. These openings are centered on an optical axis Y (an optical axis having the same reference Y is defined for each optical unit 110, 120).

The exit aperture 120B of each optical unit 110, 120 is designed to be placed in the axis of a corresponding eye of the patient.

The housing 121 houses an optical system or module (not shown) for providing different vision correction powers to the corresponding eye of the patient.

This optical system may be of any kind. In particular, it may comprise different lenses with different optical powers to be presented in front of each eye of the individual. In this embodiment, the lenses with different powers are interchanged through a manual or preferably through a motorized command. These different powers are vision correction powers for the eye of the individual placed nearby.

In the shown embodiment, the optical system preferably comprises two lenses of adjustable power, such as liquid lenses having variable spherical powers.

Said variable spherical power lens has for instance a deformable surface. The shape of this surface (in particular the radius of curvature of this surface, and hence the spherical power provided by the lens) can be controlled mechanically (for instance thanks to a ring attached to a mechanical part driven by a motor) or in a different way.

The phoropter 100 may also include a pair of independently rotatable lenses each having a cylindrical power. They may each be rotated by action of other motors of the phoropter 100.

The motors are controlled by a control unit such that the combination of the variable spherical power lens and the two cylindrical power lenses provides a desired spherical correction and a desired cylindrical correction to the patient's eye, as explained in document WO 2015/1007 303.

The phoropter 100 also comprises one or more support element 122 designed to receive the head of the individual and to hold it in a predetermined position relative to the phoropter 100. This support element 122 may for example receive the forehead of the individual. Alternatively or in addition, the phoropter could comprise an element to receive the chin of the individual.

In this embodiment, the forehead support element 122 is slidably mounted on a chassis of the phoropter 100 (said chassis 140 being screwed onto the main casing 2) along an axis parallel to the optical axis Y, so that the distance between the patient's eyes and the liquid lenses of the optical units 110, 120 is manually adjustable. To help an optometrist in adjusting the position of the support element 122 along this sliding axis, at least one of the optical units 110, 120 comprises an image sensor 180 situated on the side of the housing 121 so as to be able to acquire side images showing both the corresponding eye of the patient and the liquid lens. A calculating unit is programmed to measure on this image the distance between the eye of the patient and the corresponding liquid lens and to display the result of this measure on a screen 151 visible by the optometrist.

According to the invention, the phoropter 100 further comprises:

- moving means adapted to adjust the position of the two optical units 110, 120 relative to each other,
- a partially reflecting mirror (the second beam splitter 27) situated between the optical units 110, 120 and the screen 21 along the optical path,
- an image acquiring device directed toward the second beam splitter 27 so as to acquire images of the eyes of the individual looking at the optotype through the two optical units 110, 120, and
- an image displaying device suitable to display the acquired images.

As shown in FIGS. 1 and 2, the second beam splitter 27 is placed between the first beam splitter 26, the image acquiring device and the optical units 110, 120 in order to let the light beam emitted by the screens 21, 22 of the acuity and scene modules 20A, 20B reaching the patient's eyes and to let the image acquiring device observing these eyes.

In other words, this second beam splitter 27 is positioned such that it reflects the light coming from the optical units 110, 120 towards the image acquiring device and it let the light beam emitted by the screens 21, 22 of the acuity module 20A and of the scene module 20B passing through it.

The moving means are designed so that the two optical units 110, 120 can approach or move away from each other along an axis X that is parallel to the plane of the second beam splitter 27, so as to fit to different individual's eye distances. The two optical units 110, 120 can be moved between two extreme positions: a closest position, wherein the two optical units are in touch one another along the X axis, and a farthest position wherein they are separated by a maximum distance along this X-axis, via intermediate positions. Among these intermediate positions, a said "average position" is set such that the two cameras of the optical units 110, 120, are separated from the mean interpupillary distance of adults, for example between 64-66 mm. This axis X is here orthogonal to the optical axes Y of the liquid lenses.

As shown in FIG. 11, the moving means comprise a slider that is fixed onto the chassis 140 of the phoropter 100 and onto which each optical unit 110, 120 can slide along a single axis (the X axis).

This slider comprises a cylindrical rod 141 that is fixed to the chassis 140. It also comprises two sleeves 142 that can freely slide along the cylindrical rod 141 along the X axis.

In a first embodiment not represented in the drawings, the moving means are designed to be manually actuated.

In this embodiment, the housings 121 of the optical units 110, 120 are respectively mounted to the two sleeves 142 (preferably with a mobility of rotation around a Z axis). The moving means further comprise at least one handle enabling the optometrist to manually adjust the relative position of one of the optical units 110, 120 relative to the other one.

More specifically, the moving means can comprise two handles to manually adjust the positions of the two optical units relative to the support element 122. The handles can be formed by the housings 121 of the optical units 110, 120 if they are shaped to facilitate the gripping of these units.

In a preferred embodiment shown in FIG. 11, the moving means are motorized.

To this end, a carriage 143 holding one of the optical units 110, 120 is mounted on each sleeve 142.

The moving means comprise at least one motor suitable to adjust the relative position of the two optical units 110, 102, and a controller (here a computer 150) programmed to control the motor as a function of the images when acquired and processed to detect the positions of the patient's pupils.

More specifically, in this preferred embodiment, the moving means comprise four motors 144 able to make the two carriages 143 slide along the X axis.

A worm gear is provided between each motor 144 and one of the carriages 143. In other words, each carriage 143 is driven by a couple of motors 144 for the following reasons.

Each couple of motors allows the corresponding carriage 143 to slide along the rod (along the X axis) when the rotation of the two motors are synchronized.

This couple of motors allows this carriage 143 to pivot around a Z axis when the rotation of the two motors are not synchronized (an axis having the same reference Z is defined for each optical unit 110, 120). More specifically, to make the carriage 143 pivot around the Z axis without sliding along the X axis, the two motors have to be controlled at the same speed but in opposite directions.

To this end, each carriage comprises a first upper part fixed onto the corresponding sleeve 142, and a second lower part mounted one the first part with a mobility of rotation around the Z axis.

This second part is screwed onto the housing 121 of the corresponding optical unit 110, 120 and is provided with a gearwheel engaging the motors screws.

Thanks to the mobilities in rotation around the Z axes, the optical axis Y of the liquid lenses can be tilted relative to each other so as to be oriented in the gaze direction of each patient's eye. This mobility is useful when the near vision of the patient is tested (which requires the patient to squint when looking at the optotype).

Thanks to the mobility of sliding along the X axis, the liquid lenses can be positioned in the axes of the patient's eyes that is, at a distance from each other that depends on the interpupillary distance of the patient. We note that the distance between the optical axes Y of the liquid lenses is equal to the interpupillary distance only when these axes are parallel.

To automatically or manually adjust the distance between the two optical units 110, 120, the image acquiring device and the image displaying device are used.

In the shown embodiment, the image acquiring device comprises two cameras 132 each directed toward the second beam splitter 27 so as to acquire images of one of the eyes of the patient looking at the optotype through one of the optical units 110, 120.

In a non-represented embodiment, each camera 132 could be fixed on the carriage 143 of the corresponding optical unit 110, 120, therefore integral in translation with the corresponding optical unit 110, 120. In this variant, the optical axis of each camera would remain perpendicular to the Y optical axis of the liquid lens of the corresponding optical unit 110, 120 on the beam splitter 27 (the two axes intersecting each other on the beam splitter 27), whatever the distance separating the two optical units 110, 120 along the X axis. By perpendicular, it is meant that the two axes are orthogonal and intersect each other.

But in the shown embodiment (see FIG. 3), the two cameras are fixed to the main casing 2 so that they are not integral in translation along the X axis with the corresponding optical unit 11, 120, and their optical axes are stationary. In this configuration, there is only one position of the optical units 110, 120 wherein the optical axis of each camera remain perpendicular to the optical axes Y of the liquid lenses of the optical units 110, 120 on the beam splitter 27. This only one position of the optical units along the X axis, can be set as the above mentioned average.

In this embodiment, when the optical axes of the liquid lenses of the two optical units 110, 120 are in the average position, the cameras are well centered in these axes (in other words, the optical axis Y of each liquid lens intersects the optical axis of the corresponding camera). But when the distance between these optical axes Y varies because the optical units 110, 120 are moved away from the average position along the X axis, the optical axis Y of each liquid lens no longer intersects the optical axis of the corresponding camera and parallax phenomena appear. As explained below, these phenomena will have to be counterbalanced.

In another embodiment, the two cameras are respectively hold by the two optical units 110, 120, therefore integral in translation and in rotation with the corresponding optical unit 110, 120. In this embodiment, the optical axis of each camera remains perpendicular to the Y optical axis of the liquid lens of the corresponding optical unit 110, 120 on the beam splitter 27 (the two axes intersecting each other on the beam splitter 27), whatever the distance separating the two optical units 110, 120 along the X axis and whatever the angle between the optical units 110, 120 (this is useful when the near vision of the patient is tested, said vision requiring the patient to squint when looking at the optotype).

Preferably, each camera 132 is housed in a little protective black box so as not to be visible by the patient.

The image displaying device suitable to display the images acquired by the cameras 132 is for instance a LED or OLED or LCD or TFT screen 151. It is situated so as to be visible par the optometrist.

In the embodiment shown in FIG. 3, this screen 151 belongs to a computer 150 having another human-machine interface 152 (a keyboard and/or a mouse).

The computer 150 is connected to the cameras 132 so as to be able to display in real time an image assembly Img including the images acquired by these cameras (see FIG. 4).

The computer is programmed to help the optometrist in adjusting the distance between the optical units 110, 120.

If the moving means are of the manual type, the computer 150 is programmed to display a sight 153 having a center centered on each acquired image, at the position of the Z optical axis of each liquid lens. This sight 153 can have a cross shape or a circular shape or a square shape with a transparent interior surface.

As explained above, in the embodiment wherein the cameras 123 are fixed to the main casing 2, the positions of these sights 153 have to be calculated so as to counterbalance the parallax phenomena occurring for positions of the optical units 110, 120 different from the average position. This calculation is made on the basis of the positions of the optical units 110, 120 along the X axis, thanks to predetermined settings that associate each position of an optical unit with a position of the sight to be displayed.

To determine the positions of the optical units, the computer can acquire the angular positions of the four motors (if any) and/or use position sensors coupled to the carriages.

Then, to position the optical units 110, 120 in front of the patient's eyes, the optometrist can use the handles to force these units to slide along the rod 141 until the patient's pupils are centered within the sights 153 (center of the cross, circle, square).

If the moving means are of the motorized type, the computer 150 is programmed to automatically control the four motors so as to adjust the positions of the two optical units 110, 120 in the axes of the two patient's pupils.

To this end, the computer 150 is here programmed to:

- display the sights 153 superimposed to the acquired images,
- determine, on the acquired images Img, the position of the pupils of the patient relative to the sights 153 (for this purpose, the computer 150 is equipped with image processing functions allowing the recognition of a full black circle in an image and its position on that image along a X axis) and to
- deduce therefrom a driving instruction for each motor to position the detected full black circle representing at least the pupil of the subject (or the iris of black-eyed subjects) at the center of the sight 153.

At this stage, we can describe in more details the light beam separation box 200 shown in FIGS. 5 to 7.

This box comprises a casing in three parts: an upper part 210, an intermediate part 211 (also called "mirror support") and a lower part 212 (see FIG. 6).

The lower part 212 is designed to be mounted and screwed onto the main casing 2. It has a large opening 213 to let the light emitted by the screen 21 enter in the light beam separation box 200.

The intermediate part 211 is mounted and screwed onto the lower part 212. It has a roof prism shape, with a base opened toward said opening 213, and two main face in which the beam splitters 26, 27 are fitted.

The upper part 210 is mounted and screwed onto the intermediate part 211. It has a parallelepiped shape and houses, at one end, the convex mirror 24. Its other end is opened and shaped to apply onto the intermediate part 211, along the edge of the first beam splitter 26. The screen 22 is fixed on the upper face of this upper part 210.

The convex mirror 24 has a large thickness so that its fixation to the upper part 210 can be done in many different ways, for instance by gluing its edge to the internal face of the upper part 210.

On the contrary, the beam splitters 26, 27 have low thicknesses, lower than 5 mm.

In this embodiment, the first beam splitter 26 has a thickness of 1 mm and the second beam splitter 27 has a thickness of 2 mm.

The fixing of these beam splitters needs to be carried out so as not to generate excessive stresses on these splitters, which would otherwise have the consequence of deforming these splitters and distorting the measurements.

To avoid such deforming, each beam splitter 26, 27 is blocked on the intermediate part 211 by means of a special frame.

As shown in FIG. 8, the second beam splitter 27 has a rectangular shape. Its frame 270 has a shape similar to the shape of the edge of this splitter.

This frame 270 comprises four limbs and means for fixing this frame to the intermediate part 211.

These fixation means include two tongues 271 protruding from the external face of a first limb. These tongues 271 are designed to engage with receiving cavities provided in the intermediate part 211.

They also include, in a second limb opposed to the first one, a little opening that receives a screw 273 engaged into a washer 274 and screwed into the intermediate part 211.

The frame 270 can be made of any rigid material (plastic, steel, aluminum . . . ). It is preferably molded in one piece.

To block the second beam splitter 27, the upper face of the frame 270 is recessed along the entire contour of its internal face. Thanks to this recess, the frame 270 presents a bearing surface 275 that is plane and that is bordered by an external part of the frame. The second beam splitter 27 is housed into this recess so that it leans along its entire edge on the bearing surface 275.

For holding the second beam splitter 27 against the bearing surface 275, the frame 270 comprises at least three tongues 276 protruding from the upper face of the frame so as to sandwich the second beam splitter 27 with the bearing surface 275. Here, the frame 270 comprises four tongues 276 distributed along the first and the second limbs.

Two embodiments of the first beam splitter 26 and of its frame 260; 280 are respectively shown in FIGS. 9 and 10.

In both embodiments, the first beam splitter 26 has a rectangular shape with chamfered corners. The frame 260; 280 has a shape similar to the shape of the edge of this splitter.

In these embodiments, the frame is designed to be sandwiched between the upper part and the intermediate part of the light beam separation box 200.

To this end, as shown in FIG. 7, the frame 260 rests on a flange provided on the intermediate part 211, and four abutments in the form of pins 214 are provided on the internal face of the upper part so as to be placed against or at a little distance from the frame 260. A compressible material can be sandwiched between the pins 214 and the frame 260. In the variant where no compressible material is used, a little clearance comprised between 0.3 to 1 mm is provided between the pins 214 and the frame 260 to ensure that the latter will not be deformed when the upper part 210 and the intermediate part 211 will be screwed together.

In both embodiments, the upper face of the frame 260; 280 is recessed along the entire contour of its internal face. Thanks to this recess, the frame 260; 280 presents an internal part (a "rim") having a bearing surface 265; 285 that is flat and that is bordered by an external part of the frame. The first beam splitter 26 is housed into this recess so that it leans along its entire edge on the bearing surface 265; 285 and so that it cannot move on this flat surface.

The means for blocking the first beam splitter 26 against the bearing surface 265; 285 are different in the first embodiment and in the second embodiment.

In the first embodiment, the first beam splitter 26 does not directly lean on the bearing surface 265 of the frame 260. On the contrary, a compressible material is sandwiched between this first beam splitter 26 and the bearing surface 265. This compressible material is an elastomer foam tape that has the shape of the bearing surface 265.

To hold the first beam splitter 26 against the foam tape, the frame 260 comprises at least two flexible strips 261. Each strip is profiled and comprises a first rib designed to be fixed (for instance glued) to a limb of the frame 260, and a lip that protrudes from the internal face of the rib and that press against the upper face of the first beam splitter 26. Here, each strip 261 is made of elastomer.

In the second embodiment, the first beam splitter 26 does not directly lean on the bearing surface 285 of the frame 280, thanks to four foam pieces sandwiched between this first beam splitter 26 and the bearing surface 285.

In this second embodiment, the frame 280 comprises, projecting from the bearing surface 265, three little rings designed to receive some glue.

It also comprises four openings 282 situated on two opposite limbs, having axes parallel to the bearing surface 285 and perpendicular to the longitudinal axes of these two limbs, and also four pins 283 that are glued into these four openings 282. The end of each pin 283 is longitudinally split in two parts to pinch the first beam splitter 26 and is glued thereto.

Thanks to the glue, the first beam splitter 26 is well attached to its frame, without excessive mechanical stress.

The invention claimed is:

1. An optometry device for testing an individual's eyes, comprising:

- a main casing;
- a phoropter configured to test the individual's eyes when observing a target along an optical path, the phoropter comprising:
  - two optical units for the eyes of the individual that are mounted on the main casing, each having a housing that includes an entry on the target side and an exit aperture on the individual's side, and that houses an optical system to provide different vision correction powers to the corresponding eye of the individual,
  - a moving mechanism comprising a slider upon which the two optical units are slidably mounted to allow for adjustment of a relative position between the two optical units,
  - a partially reflecting mirror situated along the optical path, wherein the partially reflecting mirror is located upstream of the two optical units in the optical path along which light travels from the target to the individual's eyes, and
  - an image acquiring device directed toward the partially reflecting mirror so as to acquire images of the eyes of the individual looking at the target through the two optical units; and
- a display device enclosed in the main casing and configured to produce the target, said target being visible through the exit apertures of the two optical units of said phoropter, the display device comprising:

a first screen configured to display a test picture used in producing said target, a second screen configured to display a second picture, an image of the second picture being superimposed with said target at the exit apertures by way of a main partially reflecting mirror, and at least one optical element having an optical power, said optical element being movable between an active position in which the optical element is placed on an optical path of light emitted by said first screen and exiting the device through said exit apertures, and a retracted position in which the optical element remains out of said optical path, in order for the target to be produced at a variable distance from said exit apertures, wherein a single mirror support holds said main partially reflecting mirror and the partially reflecting mirror of said phoropter.

2. The optometry device according to claim 1, wherein said main partially reflecting mirror leans on a rim of a frame of a mirror support.

3. The optometry device according to claim 2, wherein said main partially reflecting mirror leans on said rim along its entire edge, a compressible material being layered between said main partially reflecting mirror and said rim.

4. The optometry device according to claim 2, wherein said main partially reflecting mirror directly leans on three or four areas projecting from said rim.

5. The optometry device according to claim 2, wherein an edge of said main partially reflecting mirror is blocked and layered by three or four pins.

6. A mirror support of the optometry device according to claim 1, comprising a casing supporting the main partially reflecting mirror and the partially reflecting mirror.

7. The optometry device according to claim 1, wherein said image acquiring device comprises two cameras, each camera being directed toward the partially reflecting mirror so as to acquire images of one of the eyes of the individual looking at the target through one of the optical units.

8. The optometry device according to claim 1, wherein said moving mechanism comprises a lever to manually adjust the relative position of the two optical units.

9. The optometry device according to claim 8, wherein the phoropter comprises a support element designed to receive a head of the individual and to hold the head in position and wherein said moving mechanism comprises two levers to manually adjust the positions of the two optical units relative to said support element.

10. The optometry device according to claim 1, wherein said moving mechanism comprises at least one motor to adjust the relative position of the two optical units, and a controller configured to process the image acquired by the image acquiring device in order to detect the positions of the individual's pupils on the image, and to control the motor as a function of the detected positions of the individual's pupils.

11. The optometry device according to claim 10, wherein the phoropter comprises a support element configured to receive a head of the individual and to hold the head in position, wherein said moving mechanism comprises two motors, and wherein the controller is configured to automatically control the motors so as to adjust the positions of the two optical units relative to said support element in axes of the individual's pupils.

12. The optometry device according to claim 1, wherein said partially reflecting mirror leans along its entire edge on a rim of a frame of a mirror support, said frame comprising three or four tongues that hold the partially reflecting mirror against said rim.

13. The optometry device according to claim 1, wherein the slider comprises a rod extending in an axis parallel to a plane of the partially reflecting mirror, and two sleeves that are freely slidable along the rod along the axis and are respectively connected to the two optical units.

14. The optometry device according to claim 1, wherein the main partially reflecting mirror and the partially reflecting mirror are located outside the respective housings of the two optical units.

15. The optometry device according to claim 1, wherein the partially reflecting mirror, the entry of the housing, and the exit aperture of the housing are arranged in the recited order from the target side to the individual's side along an optical axis of each optical unit.

* * * * *